US00PP31947P2

(12) United States Plant Patent
Van Swieten

(10) Patent No.: US PP31,947 P2
(45) Date of Patent: Jul. 7, 2020

(54) ***PHALAENOPSIS* ORCHID PLANT NAMED 'PHALFOMZYN'**

(50) Latin Name: ***Phalaenopsis* hybrid**
Varietal Denomination: 'PHALFOMZYN'

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/501,996

(22) Filed: Jul. 17, 2019

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./263.1, 311
See application file for complete search history.

*Primary Examiner* — Susan McCormick Ewoldt
*Assistant Examiner* — Karen M Redden
(74) *Attorney, Agent, or Firm* — Jondle & Associates, P.C.

(57) ABSTRACT

A new and distinct variety of *Phalaenopsis* plant named 'PHALFOMZYN', particularly characterized by having light greenish-yellow flowers with orange lips, 2 to 4 peduncles that are medium long and moderate, leaves that are oblong, and is propagated by meristem tissue culture, is disclosed.

3 Drawing Sheets

Genus and species: *Phalaenopsis* hybrid.
Variety denomination: 'PHALFOMZYN'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFOMZYN'.

The new *Phalaenopsis* plant is a product of a planned breeding program conducted by the inventor in Bleiswijk, the Netherlands. The objective of this breeding program was to create a new *Phalaenopsis* plant with numerous attractive small, light greenish-yellow, dotted flowers with orange lips, suitable for potted plant production.

The new *Phalaenopsis* plant 'PHALFOMZYN' is a result of cross-pollination made by the inventor in June 2006 in Bleiswijk, the Netherlands, of the proprietary female, or seed parent, *Phalaenopsis* hybrid '21368-02' (unpatented) with the proprietary male, or pollen parent, *Phalaenopsis* hybrid '01-1787' (unpatented).

The new *Phalaenopsis* was selected by the inventor as a single plant within the progeny of the stated cross-pollination in a controlled greenhouse in Bleiswijk, the Netherlands, in August 2009. Asexual reproduction of the new *Phalaenopsis* plant by meristem tissue culture since 2012 in Bleiswijk, the Netherlands, has demonstrated that the new variety reproduces true to type with all of the characteristics, as herein described, firmly fixed and retained through successive generations.

Plant Breeder's Rights for this variety have been applied for in the European Union on Apr. 24, 2018, by Applicant who obtained the subject matter disclosed directly from the Inventor. 'PHALFOMZYN' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, the Netherlands, and can be used to distinguish 'PHALFOMZYN' as a new and distinct variety of *Phalaenopsis* plant:

1) Light greenish-yellow flowers with orange lips;
2) 2 to 4 peduncles;
3) Peduncle is medium long and moderate; and
4) Shape of the leaf is oblong.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in April 2019. Colors in the photographs may differ from the color values cited in the detailed botanical description, which accurately describe the actual colors of the new variety.

DESCRIPTION OF THE NEW VARIETY

Figure 1:
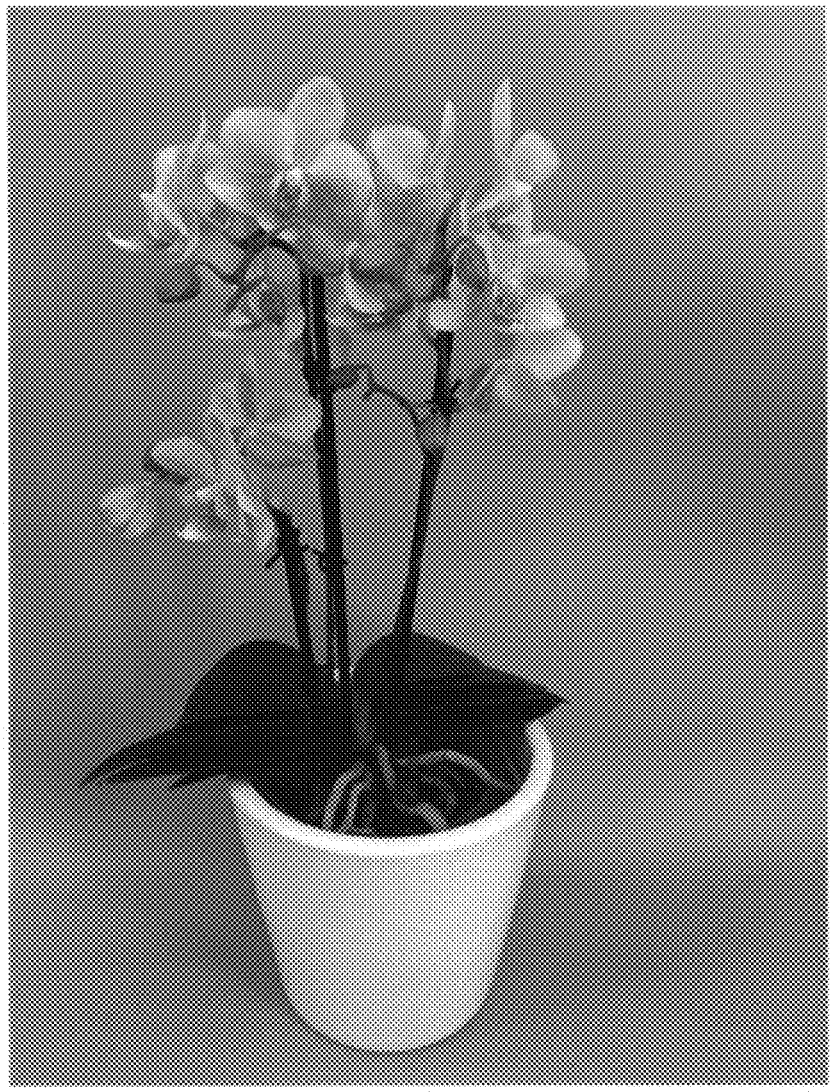
FIG. 1 shows the overall plant habit, including blooms, buds, and foliage of 'PHALFOMZYN'.
Figure 2:
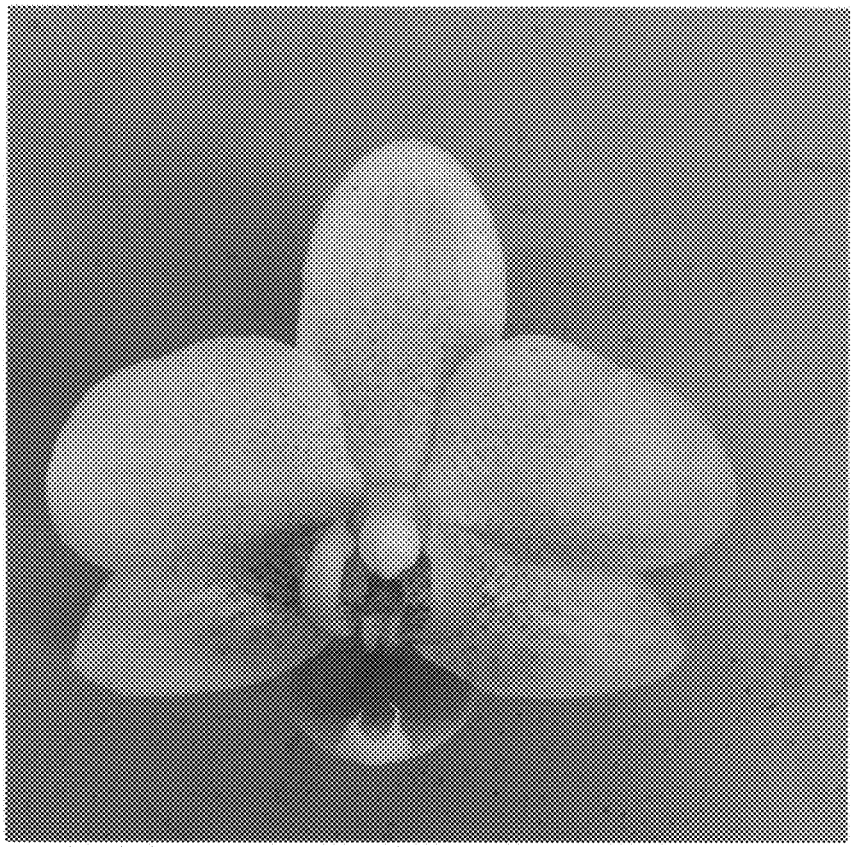
FIG. 2 shows a close-up of a flower of 'PHALFOMZYN'.
Figure 3:
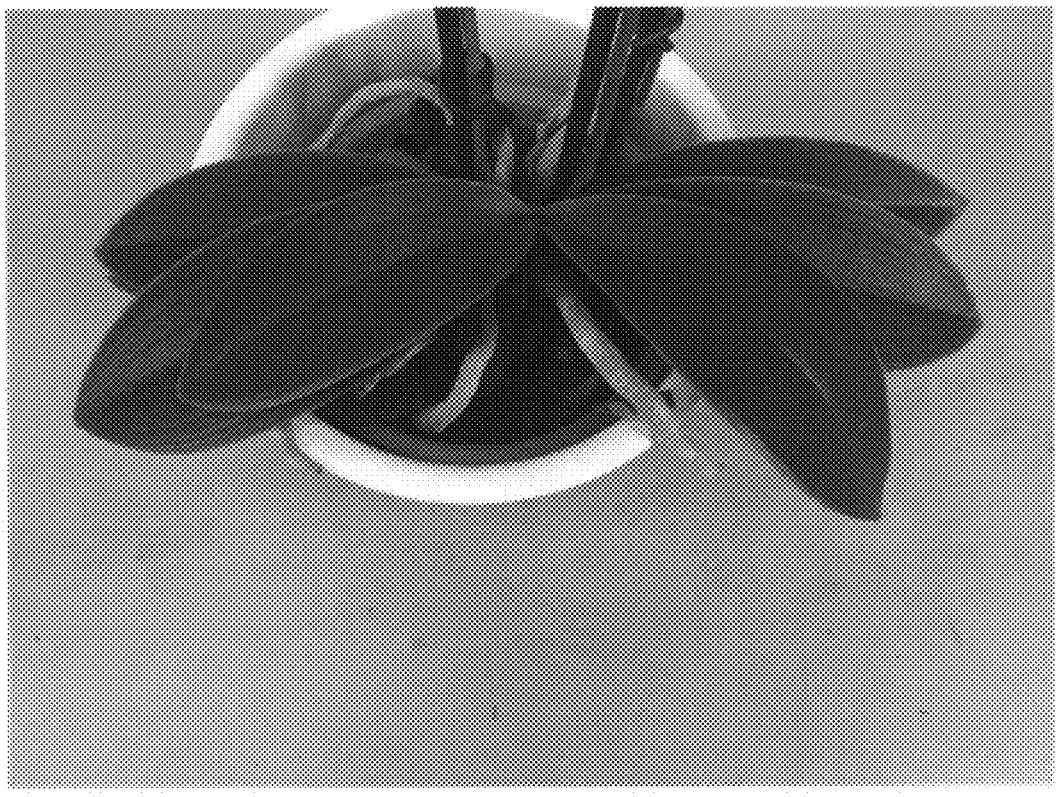
FIG. 3 shows an overhead view of the leaves of 'PHALFOMZYN'.

The following detailed description sets forth the distinctive characteristics of 'PHALFOMZYN'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is the R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in April 2019 on flowering plants which were planted in 12-centimeter (diameter) pots. After in-vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALFOMZYN'.

Parentage:

*Female parent*.—*Phalaenopsis* cultivar '21368-02' (unpatented).

*Male parent*.—*Phalaenopsis* cultivar '01-1787' (unpatented).

Propagation:

*Type*.—Meristem tissue culture.

Roots:

*Root description*.—Greyed-green (between RHS 190B and 190C) colored roots with branching lateral roots having yellow-green (RHS 144B) colored root tips.

Plant:

*Commercial crop time to flowering*.—Following asexual propagation (in-vitro), the rooted cuttings grow for 20-24 weeks. After transplantation into 12-cm pots, the plants are finished after 48 to 50 weeks.

*Growth habit of peduncle*.—Upright to slightly pendant with raceme or panicle inflorescence.

*Height* (*from soil level to top of inflorescence*).—Approximately 25.0 cm to 30.0 cm.

*Width* (*measured from leaf tips*).—About 25.0 cm to 27.0 cm.

*Vigor*.—Moderate.

Leaves:

*Mature leaves*.—Quantity per plant: 8 to 10 leaves are produced before flowering. Length (fully expanded): 12.0 cm to 14.0 cm. Width: 4.0 cm to 5.0 cm. Shape: Oblong. Base shape: Moderately elongated. Apex: Acute unequal. Leaf blade angle with the petiole (measured from the horizontal position): Between 5 degrees and 15 degrees. Leaf margin: Entire. Color: Upper surface: RHS 147A with lighter edge (RHS 146B). Lower surface: RHS 146A. Texture (both upper and lower surfaces): Rough. Thickness: 2.0 mm to 3.0 mm. Variegation: Absent. Venation: Pattern: Parallel. Color of the midvein: Upper surface: RHS 147A. Lower surface: RHS 146A.

Peduncle:

*Quantity per plant*.—2 to 4.

*Number of flowers per peduncle*.—8 to 12.

*Length*.—25.0 cm to 30.0 cm.

*Diameter*.—2.5 mm to 3.0 mm.

*Strength*.—Moderate.

*Aspect*.—Upright to slightly pendant.

*Texture*.—Smooth.

*Color*.—Yellow-green (RHS 144A).

*Internode length*.—3.5 cm to 4.5 cm.

Inflorescence description:

*Appearance*.—Upright to slightly pendant, raceme or panicle inflorescence with bilaterally symmetrical flowers that open in succession beginning with the lowermost flower.

*Number of inflorescences*.—2 to 4.

*Inflorescence size*.—Height (from base to tip): 110.0 mm to 160.0 mm.

*Flowering time*.—First flowers can be expected 10 to 11 months after planting in a 12-cm pot.

*Flower*.—Height: 45.0 mm to 50.0 mm. Diameter: 50.0 mm to 55.0 mm. Depth of lip: 16.0 mm to 18.0 mm.

*Flower longevity*.—On the plant: 12 to 16 weeks.

*Fragrance*.—Absent.

*Flower bud*.—Average size: Medium. Length: 16.0 mm to 18.0 mm. Width: 13.0 mm to 15.0 mm. Shape: Egg shaped. Color: Yellow-green (RHS N144D).

*Petals*.—Arrangement: Open/free. Shape: Semi-circular. Apex: Rounded asymmetric. Margin: Slightly undulated. Length (from base to tip): 24.0 mm to 26.0 mm. Width: 23.0 mm to 25.0 mm. Position of the broadest part of the petal: Toward the base. Color (when fully opened): Upper surface: Basic color: Light greenish-yellow (RHS 1C). Over color: Slightly very light purple (RHS 76B to 76C) at the base; small red dots (RHS 182B). Lower surface: Basic color: Light greenish-yellow (RHS 1C). Over color: Absent.

*Dorsal sepal*.—Shape: Elliptic. Apex: Obtuse emarginated. Margin: Entire. Length (from base to tip): 26.0 mm to 28.0 mm. Width: 16.0 mm to 18.0 mm. Color (when fully opened): Upper surface: Basic color: Light greenish-yellow (RHS 1C). Over color: Small red dots (RHS 182A). Lower surface: Basic color: Light greenish-yellow (RHS 1C). Over color: Slightly yellowish-green (RHS N144A) in the middle.

*Lateral sepals*.—Shape: Ovate. Apex: Obtuse asymmetric. Margin: Entire. Length (from base to tip): 27.0 mm to 29.0 mm. Width: 17.0 mm to 19.0 mm. Color (when fully opened): Upper surface: Basic color: Light yellow-green (RHS 145C). Over color: Dotted (RHS 182A to 182B) at the base. Lower surface: Basic color: Green-yellow (RHS 150C). Over color: Diluting red dots (RHS 182B).

*Labellum* (*lip*).—Whiskers: Present. Length of whiskers: 1.0 mm to 3.0 mm. Color of whiskers: White (RHS NN155C). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Undulated. Length: 12.0 mm to 14.0 mm. Width: 6.0 mm to 8.0 mm. Color: Yellow (RHS 7A) at the base and one side; striped (RHS 172A) at the base; white (RHS NN155C) toward the other side.

*Apical lobe*.—Shape: Elliptic to circular. Margin: Entire. Length: 17.0 mm to 19.0 mm. Width: 15.0 mm to 17.0 mm. Color: Orange (RHS 172C to 172D) at the base; greenish-yellow (RHS 2B) on sides; slightly very light purple (RHS 76C) in the middle and white (RHS NN155C) toward whiskers.

*Callus*.—Average size: Small. Height: 3.0 mm to 4.0 mm. Length: 3.0 mm to 4.0 mm. Width: 2.0 mm to 3.0 mm. Color: Yellow (RHS 15A); dotted (RHS 175C).

Reproductive organs:

*Column*.—Length: 8.0 mm to 10.0 mm. Diameter: 3.0 mm to 4.0 mm. Color: Very light purple (RHS 76C) at the base and white (RHS NN155C).

*Pollinia*.—Quantity: 2. Diameter: 0.5 mm to 0.7 mm. Color: Orange (RHS 24A).

*Ovary*.—Length: 7.0 mm to 9.0 mm. Diameter: 1.4 mm to 1.6 mm. Color: Light yellow-green (RHS 145C).

*Pedicel*.—Length: 23.0 mm to 25.0 mm. Diameter: 1.8 mm to 2.0 mm. Color: Slightly yellow-green (RHS 144A) at the base; light yellow-green (RHS 145B) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALFOMZYN' differs from female parent plant '21368-02' (unpatented) in that 'PHALFOMZYN' has flowers with an upper surface basic color of light greenish-yellow (RHS 1C) and no fragrance, whereas '21368-02' has flowers with an upper surface basic color of yellow (RHS 9C) and a fragrance.

'PHALFOMZYN' differs from male parent plant '01-1787' (unpatented) in that 'PHALFOMZYN' has flowers with an upper surface basic color of light greenish-yellow and a dotted pattern, whereas '01-1787' has flowers with an upper surface basic color of white and a striped and edged pattern. Additionally, 'PHALFOMZYN' has larger flowers than '01-1787'.

'PHALFOMZYN' is most similar to the commercial *Phalaenopsis* plants named 'PHALCUWIM' (U.S. Plant Pat. No. 26,138) and 'PHALGALYI' (U.S. Plant Pat. No. 31,051). 'PHALFOMZYN' differs from the commercial variety 'PHALCUWIM' in that 'PHALFOMZYN' has yellow-green peduncles and calluses with a main color of yellow, whereas 'PHALCUWIM' has brown peduncles and calluses with a main color of orange. Additionally, 'PHALFOMZYN' has smaller flowers than 'PHALCUWIM'.

'PHALFOMZYN' differs from the commercial variety 'PHALGALYI' in that 'PHALFOMZYN' has white whiskers and elliptic to circular apical lobes, whereas 'PHALGALYI' has greenish-yellow whiskers and ovate apical lobes.

I claim:

1. A new and distinct variety of *Phalaenopsis* plant named 'PHALFOMZYN', substantially as described and illustrated herein.

* * * * *